United States Patent [19]

Hahn et al.

[11] Patent Number: 5,128,320
[45] Date of Patent: Jul. 7, 1992

[54] METHOD OF RESTORING NORMAL GROWTH, WEIGHT GAIN OR LEAN BODY MASS IN PATIENTS WITH GLUCOCORTICOID EXCESS BY ADMINISTERING IGF-I

[75] Inventors: Theodore J. Hahn, Encino; Christopher G. Rudman, San Francisco, both of Calif.

[73] Assignee: Genentech, Inc., South San Francisco, Calif.

[21] Appl. No.: 466,899

[22] Filed: Jan. 18, 1990

[51] Int. Cl.$^5$ .............................. A61K 37/36
[52] U.S. Cl. ....................... 514/12; 514/21
[58] Field of Search .................... 514/12, 21

[56] References Cited

U.S. PATENT DOCUMENTS 4,988,675  1/1991  Froesch et al. ............. 514/12

FOREIGN PATENT DOCUMENTS 327503  8/1989  European Pat. Off. .
0434625  6/1991  European Pat. Off. .

OTHER PUBLICATIONS

Fagin et al. (Jun. 1989) Endocrine Soc. Annual Meeting, Abstraact No. 1666.
Luo et al. (Jul. 1989) Endocrinology 125:165–171.
Scheiwiller et al. (1986) Nature 323:169–171.
Schalch et al. (1989, Apr. 28) Biochem. Biophys. Res. Comm. 160(2):795–800.
Guler et al., N. Engl. J. Med., 317(3):137–140 (1987).
Guler et al., Endocrinology, 118: Supp. 129 abstract.
Skottner et al., Endocrinology, 124(5):2519–2526 (1989).
van Buul-Offers et al., Pediatr. Res. 20(9):825–837 (1986).
Loeb, N. Engl. J. Med. 295(10):547–552 (1976).
McArthur et al., Mayo Clin. Proc. 47:318–326 (1972).
Monro, in Mammalian Protein Metabolism, eds. Monro and Allison (Academic Press, Inc., New York, 1964) p. 381.
Soyka and Crawford, J. Clin. Endocrinol. Metab., 25:469–475 (1965).
Nicholson et al., Neuroendocrinology, 39:343–349 (1984).
Luo and Murphy, Endocrinology, 125(1):165–171 (1989).
Wehrenberg et al., Science 221:556–558 (1983).
Oosterom et al., Endocrinology, 113(2):735–741 (1983).
Hofert et al., Metabolism, 38(6):594–600 (1989).
Conover et al., In Vitro Cell. & Dev. Biol., 25(6):521–527 (1989).
Elders et al., Am. J. Dis. Child., 129:1393–1396 (1975).
Unterman & Phillips, J. Clin. Endocrin. & Metab., 61:618–626 (1985).
Reid et al., Clin. Endocr., 30:347–353 (1989).

Primary Examiner—Robert A. Wax
Assistant Examiner—Richard C. Ekstrom
Attorney, Agent, or Firm—Janet E. Hasak

[57] ABSTRACT

A method is disclosed for at least partially restoring normal growth, weight gain, and lean body mass of a mammal afflicted with glucocorticoid excess. This method comprises the administration to the mammal of an effective amount of IGF-I. Preferably, the mammal is a child and the IGF-I is native-sequence or brain IGF-I.

15 Claims, 2 Drawing Sheets

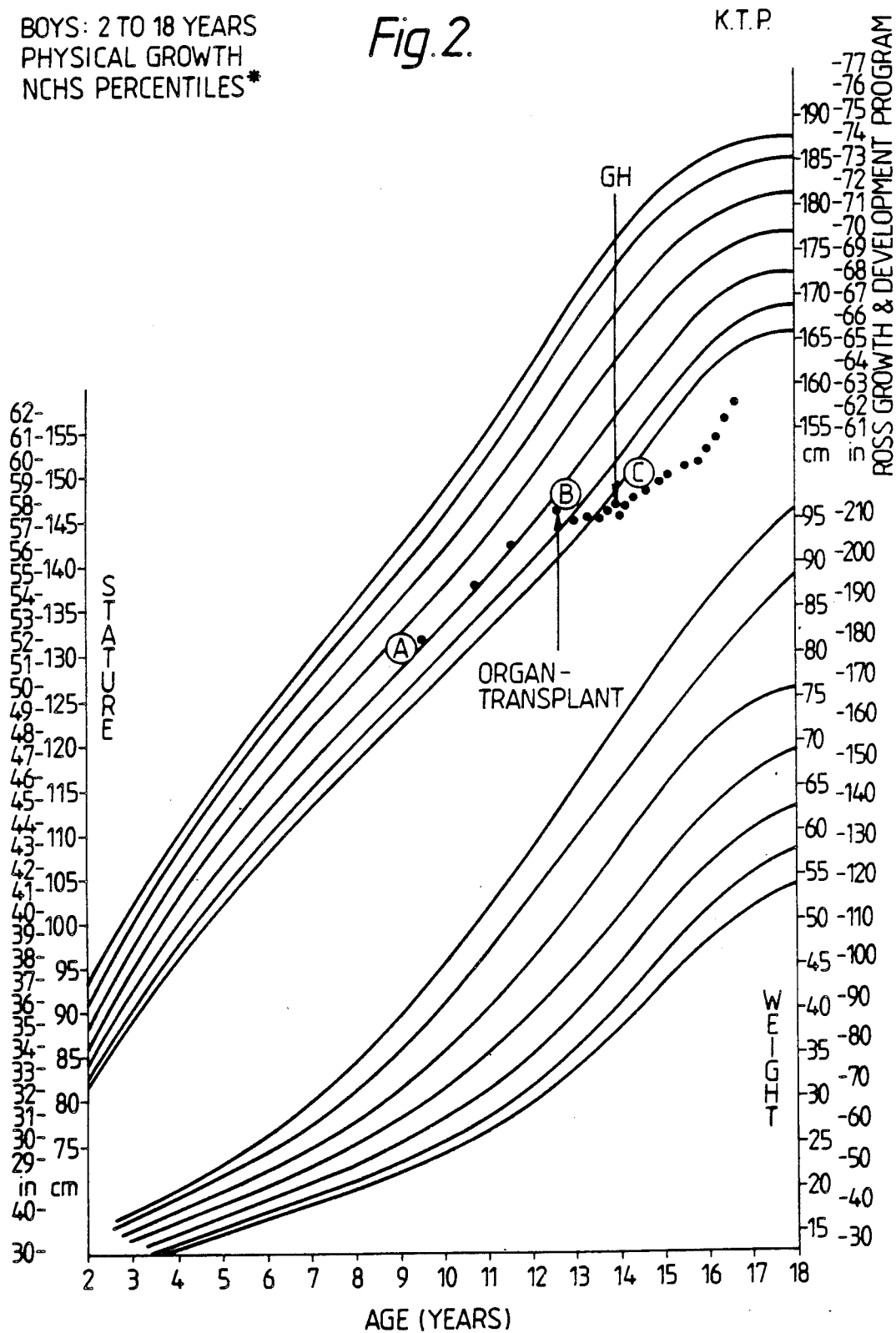

METHOD OF RESTORING NORMAL GROWTH, WEIGHT GAIN OR LEAN BODY MASS IN PATIENTS WITH GLUCOCORTICOID EXCESS BY ADMINISTERING IGF-I

BACKGROUND OF THE INVENTION

1. Field of the Invention

This invention relates to a method of at least partially restoring normal growth and weight gain as well as lean body mass in patients with glucocorticoid excess exhibiting a retarded growth rate or weight loss.

2. Description of Related Art

Insulin-like growth factor I (IGF-I) is a polypeptide naturally occurring in human body fluids, for example, blood and human cerebral spinal fluid. Most tissues and especially the liver produce IGF-I together with a specific IGF-binding protein Both of these molecules are under the control of human growth hormone (GH). Like GH, IGF-I is a potent anabolic protein. See Tanner et al., *Acta Endocrinol.*, 84: 681–696 (1977); Uthne et al., *J. Clin. Endocrinol. Metab.*, 39: 548–554 (1974)). IGF-I has been isolated from human serum and produced recombinantly See, e.g., EP 123,228 and 128,733.

Various biological activities of IGF-I have been identified. Researchers have found that an intravenous bolus injection of IGF-I lowers blood glucose levels in humans. See Guler et al., *N. Engl. J. Med.*. 317: 137–140 (1987). Additionally, IGF-I promotes growth in several metabolic conditions characterized by low IGF-I levels, such as hypophysectomized rats (Guler et al., *Endocrinology*, 118: Supp 129 abstract,), diabetic rats (Scheiwiller et al., *Nature*, 323: 169–171 (1986)), and dwarf rats (Skottner et al., *Endocrinology*, 124: 2519–2526 (1989)). The kidney weight of hypophysectomized rats increases substantially upon prolonged infusions of IGF-I subcutaneously. Guler et al., *Proceedings of the 1st European Congress of Endocrinology*, 103: abstract 12-390 (Copenhagen, 1987). The kidneys of Snell dwarf mice and dwarf rats behaved similarly. van Buul-Offers et al., *Pediatr. Res.*, 20: 825–827 (1986); Skottner et al., supra. An additional use for IGF-I is its administration to improve glomerular filtration and renal plasma flow. See EP 327,503 published Aug. 9, 1989.

Human growth hormone is a single-chain polypeptide consisting of 191 amino acids (molecular weight 21,500). Disulfide bonds link positions 53 and 165 and positions 182 and 189. Niall, *Nature, New Biology*, 230: 90 (1971). GH is a potent anabolic agent, especially due to retention of nitrogen, phosphorus, potassium, and calcium. Among its most striking effects in hypopituitary (growth hormone deficient) subjects is accelerated linear growth of cartilage resulting in increased stature. Kaplan, *Growth Disorders in Children and Adolescents* (Springfield, Ill.: Charles C. Thomas, 1964). These effects on bone and the lengthening epiphysis could be a result of increased protein synthesis by GH, suggesting a direct role for hormonal supplementation in growth retardation.

Hypercortisolism in humans, whether from Cushing's disease or chronic glucocorticoid therapy, is associated with a number of negative catabolic effects, including reduced growth velocity (Loeb, *N. Eng. J. Med.*, 295: 547 (1976), McArthur et al., *Mayo Cliln. Proc.*, 47: 318 (1972)) and lean body mass (Munro, in *Mammalian Protein Metabolism*, eds. Munro and Allison (Academic Press, Inc., New York, 1964), p. 381). Glucocorticoids are known to retard linear growth in normal and hypopituitary children and rats (Soyka et al., *J. Clin. Endocrinol. Metab.*, 25: 469 (1965); Loeb, supra, McArthur et al., supra, Nicholson et al., *Neuroendocrinology*, 39: 343 (IgB4), Luo and Murphy, *Endocrinology*, 125: 165 (1989)).

The potential of anabolic proteins, such as GH and IGF-I, to counteract the tissue wasting and statural deficits that attend chronic glucocorticoid exposure is poorly understood. There appear to be multiple sites of glucocorticoid action on the endocrine axis governing linear growth. Dexamethasone enhances GH release in vitro (Wehrenberg et al., *Science*, 221: 556 (1983)), and in vivo (Oosterom et al., *Endocrinology*, 113: 735 (1983)). Yet, dexamethasone reduces GH-induced IGF-I mRNA and has variable effects on serum IGF-I concentrations In vivo (Luo and Murphy, supra).

A putative IGF-I inhibitor has been identified in children treated with glucocorticoids. Glucocorticoids cause a diabetes-induced rise in the level of IGF-I inhibitor found in the rat. Hofert et al., *Metabolism*, 38: 594 (1989).

Recently, investigators have reported that IGF-I prevents glucocorticoid-induced weight loss; however, IGF-I treatment did not affect kidney weight. Fagin et al., *Endocrine Soc. Annual Meeting* Abstract No. 1666 (June 1989).

It is an object of the present invention to provide an agent that at least partially reverses the retardation of growth in normal and hypopituitary children that accompanies chronic treatment with glucocorticoids or Cushing's disease.

It is another object to provide a drug that at least partially counteracts the retardation in lean body mass of patients with glucocorticoid excess, whether children or adults.

It is a further object to provide an agent that antagonizes the diabetogenic effect and minimizes the osteopenic effects of glucocorticoids in patients undergoing chronic glucocorticoid treatment.

These and other objects will be apparent to those of ordinary skill in the art.

SUMMARY OF THE INVENTION

Accordingly, the present invention provides a method for at least partially restoring normal growth, weight gain, and lean body mass of a mammal with glucocorticoid excess comprising administering to the mammal an effective amount of IGF-I.

The unexpected advantage is that IGF-I, but not GH (despite clinical predictions), at least partially overcomes the catabolism induced by at least two weeks of treatment with glucocorticoids. Further, clinical data show that in some immunosuppressed pediatric patients GH does not uniformly increase growth rate. Administration of IGF-I also partially reverses reduction in kidney size of the mammal caused by the glucocorticoid treatment at higher doses and/or for longer glucocorticoid treatment times. Thus, IGF-I prevents at least partial reduction in normal renal function associated with decrease in organ size. Further, IGF-I is expected to reverse or minimize the adverse diabetogenic effect (which would be independently exacerbated by GH) and osteopenic effect resulting from excess glucocorticoids.

BRIEF DESCRIPTION OF THE DRAWINGS

FIG. 2 is a growth curve (dotted line) for a boy who grows at about the 25 percentile (A to B), undergoes a renal transplant (B) followed by glucocorticoid therapy, during which growth ceases, and then is treated with GH (C).

DESCRIPTION OF THE PREFERRED EMBODIMENTS

A. Definitions

Figure 1:
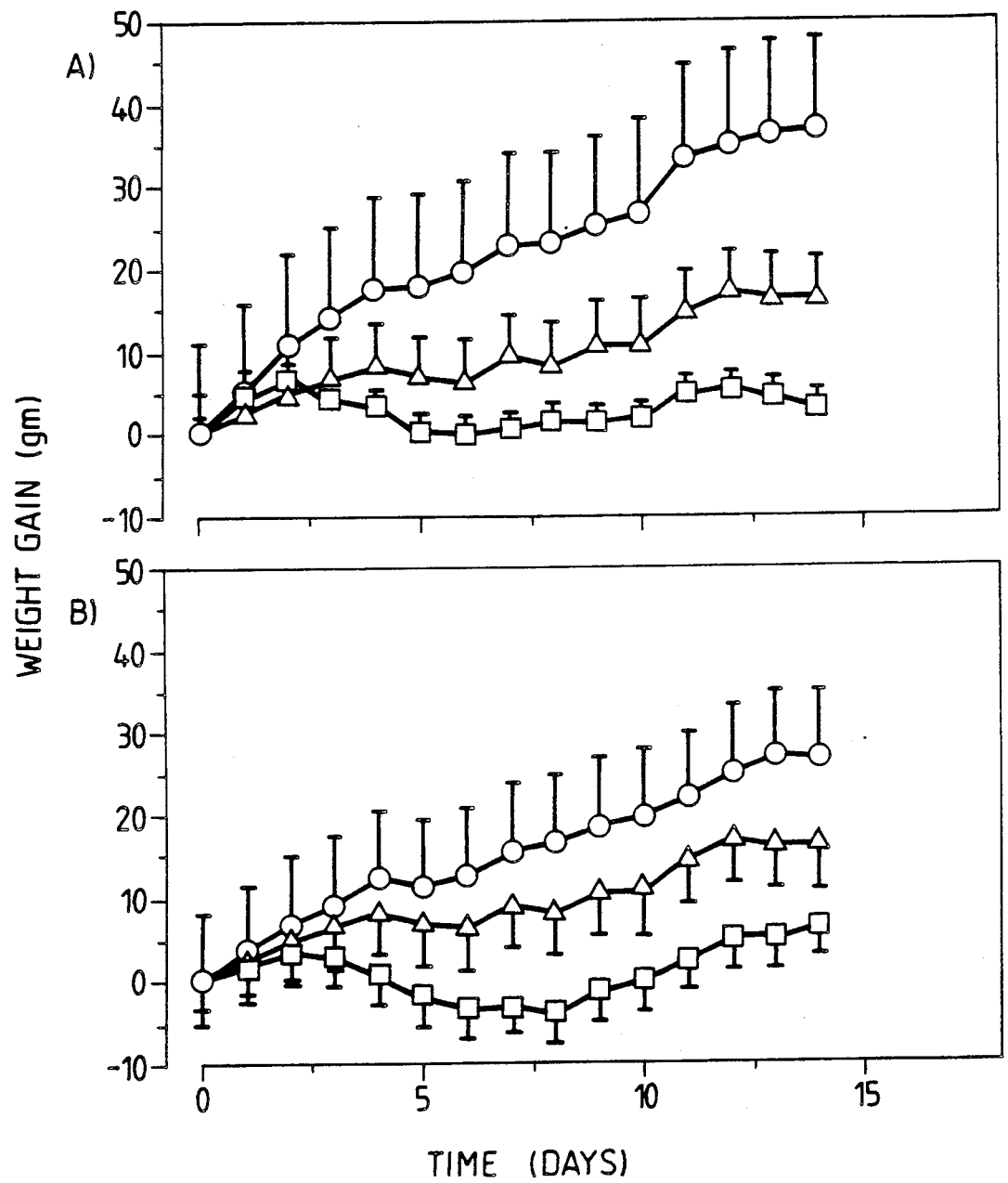
FIG. 1 represents a graph of the daily body weight gain in dexamethasone-treated rats of IGF-1 (circles), excipient (triangles), and GH (squares) at A) high dose (2.4 mg/kg/day) and B) low dose (0.8 mg/kg/day).

As used herein, the expression "glucocorticoid excess" refers to patients afflicted with a condition associated with chronic exposure to above-normal levels of glucocorticoids. As a result, these patients can be characterized as having high blood levels of glucocorticoids. Examples include excessive secretion of adrenocortical hormones such as cortisol in Cushing's disease, or chronic exposure to glucocorticoids such as dexamethasone or prednisone used as antiinflammatory agents in many clinical scenerios such as renal transplantations.

As used herein, "mammal" includes humans as well as animals. The term "non-adult mammals" refers to mammals that are between infancy and puberty, i.e., those that have not yet reached full growth potential.

As used herein, "IGF-I" refers to IGF-I from any species, including bovine, ovine, porcine, equine, and preferably human, in native-sequence or in variant form, or from any source, whether natural, synthetic, or recombinant. Preferred is recombinant human IGF-I, prepared, e.g., by the process described in EP 128,733 published Dec. 19, 1984. The most preferred variants are those described in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus The most preferred variant has the first three amino acids from the N-terminus deleted (i.e., brain IGF).

As used herein, the term "weight gain" refers to gain in total body weight as is desired for children who have not reached adulthood. "Normal growth" refers to the dynamics of growth experienced by an individual during childhood and adolescence as depicted by a normal growth curve. Restoration of normal growth patterns would allow the patient to approach a more satisfactory growth curve. "Lean body mass" refers to the normal weight of an adult, taking into account the height and bone structure of the adult.

B. Modes for Carrying Out the Invention

The IGF-I is administered to the mammal by any suitable technique, preferably parenterally, intranasally, orally, or subcutaneously. The specific route of administration will depend, e.g., on the medical history of the patient. Examples of parenteral administration include intramuscular, intravenous, intraarterial, and intraperitoneal administration. Most preferably, the administration is by continuous infusion, or by intravenous or subcutaneous means (single bolus or by slow-release depot formulation).

The IGF-I compositions to be used in the therapy will be formulated and dosed in a fashion consistent with good medical practice, taking into account the clinical condition of the individual patient, the site of delivery of the IGF-I composition, the method of administration, the scheduling of administration, and other factors known to practitioners. The "effective amount" for purposes herein is thus determined by such considerations.

As a general proposition, the total pharmaceutically effective amount of the IGF-I administered parenterally per dose will be in the range of about 1 μg/kg/day to 10 mg/kg/day, of patient body weight, although, as noted above, this will be subject to a great deal of therapeutic discretion. More preferably, this dose is at least 0.5 mg/kg/day, and most preferably at least 1 mg/kg/day. If given continuously, the IGF-I is typically administered at a dose rate of about 1 μg/kg/hour to about 50 μg/kg/hour, either by 2-4 injections per day or by continuous subcutaneous infusions, for example, using a minipump. The key factor in selecting an appropriate dose is the result obtained, as measured by increases in body weight gain, lean body mass, or growth approximating the normal range or by other criteria as deemed appropriate by the practitioner.

The IGF-I is also suitably administered by sustained release systems. Suitable examples of sustained release compositions include semi-permeable polymer matrices in the form of shaped articles, e.g., films, or microcapsules. Sustained release matrices include polylactides (U.S. Pat. No. 3,773,919, EP 58,481), copolymers of L-glutamic acid and gamma-ethyl-L-glutamate (U. Sidman et al., Biopolymers, 22, 547–556 (1983)), poly(2-hydroxyethyl methacrylate) (R. Langer et al., J. Biomed. Mater. Res., 15: 167–277 (1981), and R. Langer, Chem. Tech., 12: 98–105 (1982)), ethylene vinyl acetate (R. Langer et al., Id.) or poly-D-(−)-3-hydroxybutyric acid (EP 133,988). Sustained release IGF-I compositions also include liposomally entrapped IGF-I. Liposomes containing IGF-I are prepared by methods known per se: DE 3,218,121; Epstein et al., Proc. Natl. Acad. Sci. U.S.A., 82: 3688–3692 (1985); Hwang et al., Proc. Natl. Acad. Sci. U.S.A., 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal IGF-I therapy.

For parenteral administration, the IGF-I is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, nitrate, and other organic acid salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium, and/or nonionic surfactants such as Tween, Pluronics, or PEG.

The IGF-I is typically formulated in such vehicles at a concentration of about 0.1 mg/ml to 100 mg/ml at physiological pH. It will be understood that use of certain of the foregoing excipients, carriers, or stabilizers will result in the formation of IGF-I salts.

IGF-I to be used for therapeutic administration must be sterile. Sterility is readily accomplished by filtration through sterile filtration membranes (e.g., 0.2 micron membranes).

Therapeutic IGF-I compositions generally are placed into a container having a sterile access port, for example, an intravenous solution bag or vial having a stopper pierceable by a hypodermic injection needle.

IGF-I ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IGF-I solution, and the resulting mixture is lyophilized. The infusion solution is prepared by reconstituting the lyophilized IGF-I using 5 ml of sterile water, Ringer's solution, or at least 0.01 M acetic acid.

The invention will be more fully understood by reference to the following examples. They should not, however, be construed as limiting the scope of the invention. All literature and patent citations are expressly incorporated by reference.

EXAMPLE I

I. Protocol

Intact male Sprague Dawley rats (Charles River, Portage, Mich.) were housed three per cage and fed ad libitum and with free access to drinking water. The environment was maintained at a constant ambient temperature and light cycle (24-hour light cycle, 12 hours light, 12 hours dark). At the time of the minipump implantation, the body weights were 240-260 g for Study A and 145-160 g for Study B. The rats were anesthetized intramuscularly with the anaesthetic gas designated Metofane ™ (methoxyflurane, Pittman-Moore Inc., Washington Crossing, N.J.) in Study A and Ketamine HCl (Aveco, Ft. Dodge, Iowa)/Rompun HCl (Xylazine, Rugy Labs, Rockville Center, N.Y.) in Study B. Osmotic minipumps were inserted subcutaneously in a dorsal neck incision that was then closed with silk sutures. In Study A, two Alza pumps Model 2001 (Lot 62933: mean pumping rate $0.97 \mu l/hr$; mean fill volume $212 \mu l$) were used. In Study B, one Alza pump Model 2ML2 (Lot 55978: mean pumping rate 4.41 $\mu l/hr$; mean fill volume 2153 $\mu l$) was implanted into each rat. In Study A, each rat also received an intraperitoneal injection of 1 ml of oxytetracycline (Liquamycin, Pfizer) at a dose of 10 mg/kg.

The rats were weighed daily between eight and ten a.m., and all animals remained healthy throughout the experiment. At the end of the study, the rats were disabled by $CO_2$ (Study A) or by ketamine-xylazine (Study B). Blood was taken by cardiac puncture The minipumps were removed at necropsy, placed in pairs in test tubes and immersed in 1.271 ml of the buffer used in the IGF-I radioimmunoassay (RIA). These tubes were capped and refrigerated for two days. The flow moderator was then removed and the contents of the minipumps aspirated using the needle supplied by the pump manufacturers and a 50-microliter Hamilton syringe. Each pump was then flushed twice with an equal volume of the immersion buffer and discarded. A second dilution of the pump contents was made consisting of a 1:50 dilution or 40 microliters to 1.96 ml of an RIA buffer (0.1% gelatin in phosphate buffered saline, 0.05% polysorbate 20, and 0.01% thimerasol) or of a radioreceptor assay (RRA) buffer (50 mM TrisHCl, 0.5% bovine serum albumin, and 0.02% sodium azide). This was followed by an identical further 1:50 dilution. The excipient pumps were carried through this procedure to check for mis-implanted pumps and to ensure that an assay blank reading was achieved with the excipient. All samples were assayed in duplicate in each assay. For the larger-sized pumps, the remaining volume was all removed and weighed prior to submission to the IGF-I or GH assays.

The kidneys were dissected and weighed fresh. Blood glucose (coupled hexokinase procedure), triglyceride, and total protein were determined on a Monarch 2000 Chemical Systems Instrument (Allied Instrument Laboratories, Lexington, Mass.). Total serum IGF-I was measured after acid-ethanol extraction (Daughaday et al., *J. Clin. Endocrinol. Metab.*, 51: 781 (1980)) by a conventional RIA using the RIA buffer described above, recombinant human IGF-I (EP 128,733 published December 19, 1984) as the standard, and a rabbit anti-IGF-I polyclonal antiserum supplied by Dr. P. Gluckman (New Zealand). The acceptable range was 1.25 to 40 ng/ml), while intra- and interassay variability were 5-9% and 6-15%, respectively. Insulin was assessed by a conventional RIA using a rat insulin standard obtained from Eli Lilly, Indianapolis, Ind.

Statistical comparisons were determined by an analysis of variance with a subsequent Duncan's Multiple Range Test. A P value of less than 0.05 was considered significant. All data were represented as the mean ± standard deviation (SD) of 5-8 animals per group.

II. Study A

Sixteen rats each were implanted with two osmotic pumps containing excipient (i.e., citrate buffer for IGF-I and mannitol phosphate for GH); 16 rats had pumps containing recombinant human IGF-I (EP 128,733 published December 19, 1984), dissolved at 5 mg/ml in 1 ml citrate buffer; and 16 rats had pumps containing recombinant human GH (U.S. Pat. No. 4,755,465 issued Jul. 5, 1988) at 5 mg/ml. The total doses were 0.98 and 1.2 mg/kg/day for IGF-I and GH, respectively. Half of the animals were treated with dexamethasone (4 mg/ml, TechAmerica, Lot 8167) in their drinking water (0.5 mg/l) immediately following surgery. The animals were housed so that each cage contained one animal from each of the minipump treatments.

III. Study B

In this study of two-weeks duration, the dexamethasone dose was increased to 1.0 mg/l water and the GH and IGF-I doses were increased so that the pumps delivered 0.8 or 2.4 mg/kg/day of each of IGF-I and GH as described above. Another group received a combination of the lower doses of both IGF-I and GH. Due to the use of the larger osmotic pumps, only one pump per animal was needed. One animal was excluded from the low GH group of Study B because the minipump failed. The actual amount of IGF-I or GH delivered was estimated by removing the remaining fluid from the pumps at the end of the study. For GH, these values were 374±30, 110±9, and 124±8 µg/rat/day for the high dose, low dose, and low dose plus IGF-I dose, respectively, close to the expected doses of 360, 120, and 120 µg/rat/day, respectively. For IGF-I, the measured levels of 349±74, 126±12, and 113±8 µg/rat/day for the high dose, low dose, and low dose plus GH dose, respectively, were close to the expected doses of 360, 120, and 120 µg/rat/day, respectively.

IV. Results

A. Body Weights

Study A

All animals survived for the duration of the study. Starting body weights were similar and were as follows (water/pump contents, weight in grams, mean SD): Control/excipient, 252±6; control/IGF-I, 246 14; control/GH, 250±8; dexamethasone/excipient, 250±8; dexamethasone/IGF-I, 242±10; dexamethasone/GH, 254±7.

The daily cumulative body weight gains are listed in Table 1.

weight gain, while GH enhanced the negative effect of dexamethasone.

Study B

The initial body weights in the groups were similar (water/pump contents, mean SD weight in grams): control/excipient, 172 4; dexamethasone/excipient, 170±5; dexamethasone/IGF-I high and low doses, 169±5 and 170±4; dexamethasone/GH high and low doses, 171±5 and 170±2; dexamethasone/IGF-I+GH, 173±5.

The daily weight increments for the dexamethasone-treated rats are illustrated in FIG. 1. Table 2 shows the effect of dexamethasone and the combination of IGF-I and GH on body weight increment. As with Study A, the dose of dexamethasone used produced animals that had markedly retarded weight gain. Both doses of IGF-I were effective in partially restoring, while GH treatment further reduced, body weight gain.

TABLE 2

The Effect of Dexamethasone and the Combination of GH and IGF-I on Body Weight Increment (g)*

| Days | Control Excipient | Dexamethasone** | |
|---|---|---|---|
| | | Excipient | IGF-I + GH |
| 1 | 7.1 ± 1.7 | 2.6 ± 2.2 | 2.3 ± 1.6 |
| 2 | 17.0 ± 1.1 | 4.87 ± 1.9 | 5.3 ± 2.6 |
| 3 | 25.0 ± 1.6 | 6.6 ± 2.1 | 5.9 ± 3.0 |
| 4 | 33.0 ± 2.1 | 8.3 ± 2.8 | 3.9 ± 3.3*** |
| 5 | 39.9 ± 4.3 | 6.9 ± 2.6 | 4.6 ± 2.3 |
| 6 | 47.0 ± 3.7 | 6.4 ± 2.4 | 3.9 ± 2.9 |
| 7 | 53.9 ± 3.3 | 9.4 ± 2.9 | 6.4 ± 2.1 |
| 8 | 60.7 ± 5.0 | 8.2 ± 1.5 | 5.6 ± 2.3 |
| 9 | 68.0 ± 7.4 | 10.7 ± 1.9 | 7.9 ± 2.5 |
| 10 | 74.7 ± 7.2 | 10.8 ± 1.8 | 8.8 ± 4.0 |
| 11 | 83.8 ± 8.7 | 14.6 ± 2.7 | 14.6 ± 4.5 |
| 12 | 90.2 ± 8.5 | 17.1 ± 4.0 | 17.3 ± 6.0 |
| 13 | 92.9 ± 10.1 | 16.4 ± 2.9 | 18.5 ± 6.4 |
| 14 | 103.0 ± 9.0 | 16.2 ± 2.4 | 19.9 ± 5.2 |

Statistics
*The mean ± SD (n = 6) for Study B is represented.
**From Day 1, Dex suppressed weight gain in both the excipient and IGF-I + GH groups.
***$P < 0.05$ versus Dex - Excipient group.

TABLE 1

Body Weight Increment (g) after IGF-I and GH in Dexamethasone (Dex) Treated Rats

| | Control | | | Dexamethasone | | |
|---|---|---|---|---|---|---|
| Day | Excipient # | IGF-I | GH | Excipient # | IGF-I | GH |
| 1 | 2.12 ± 4.7$^a$ | 7.24 ± 5.64 | 10.3 ± 3.9$^a$ | 0.03 ± 2.33 | 4.55 ± 2.53 | 6.52 ± 4.16 |
| 2 | 12.5 ± 50.0$^{a, b}$ | 20.1 ± 6.3$^a$ | 19.7 ± 2.7$^b$ | 7.55 ± 2.97$^{c, d}$ | 13.5 ± 4.4$^c$ | 12.9 ± 4.5$^d$ |
| 3 | 17.0 ± 4.0 | 22.6 ± 5.0 | 22.3 ± 3.6 | 4.99 ± 3.35 | 9.70 ± 4.27 | 6.81 ± 4.90 |
| 4 | 21.7 ± 5.9 | 27.6 ± 7.1 | 27.0 ± 3.6 | 4.09 ± 3.87 | 8.22 ± 5.73 | 1.58 ± 5.13 |
| 5 | 29.0 ± 5.1 | 34.0 ± 6.0 | 32.3 ± 3.2 | 6.38 ± 5.70 | 10.6 ± 6.4 | 0.14 ± 5.65 |
| 6 | 34.2 ± 6.3 | 40.4 ± 8.4 | 36.6 ± 3.7 | 6.27 ± 5.93 | 9.29 ± 9.27 | −1.59 ± 5.79 |
| 7 | 39.9 ± 6.4 | 48.1 ± 8.9 | 45.4 ± 4.2 | 10.0 ± 6.5$^a$ | 12.1 ± 10.2 | 1.01 ± 6.66$^a$ |

Statistics:
The # indicates that the dexamethasone/excipient treated group differed from the control/excipient group on all days. Identical letter superscripts for a given day indicates that the two groups are different from each other. The mean ± SD (n = 8) for Study A is represented.

In the rats not treated with dexamethasone, IGF-I increased the weight gain only on day two, whereas GH was effective on both day one and two. Dexamethasone by itself markedly lowered the daily body weight gain throughout the seven-day study. On day two of dexamethasone treatment, both IGF-I and GH increased the weight gain compared to the rats treated with dexamethasone alone. In contrast, GH-treated animals gained less weight on day 7 than either dexamethasone- or dexamethasone plus IGF-I-treated rats.

From day 4 to 7 in the dexamethasone groups, there was an insignificant trend for IGF-I to induce some In conclusion, both IGF-I and GH partially protected body weight gain during the first days of the lower dose of glucocorticoid, whereas only IGF-I exhibited this early protection at a higher dose of dexamethasone. The most intriguing finding is that IGF-I infusion maintained this weight-promoting activity for the remainder of the fourteen days, while the early effect of GH was eventually reversed. The combination of GH and IGF-I yielded a weight gain greater than that of GH and less than that of IGF-I alone.

B. Kidney Weight

Study A

Absolute kidney weights at sacrifice are represented in Table 3.

weight loss. As with Study A, GH administration had no effect on kidney weight.

The kidney-to-body weight ratios confirmed the findings of Study A (Table 4). The kidney-to-body weight ratios were increased by dexamethasone alone. Both

TABLE 3

The Effect of Dexamethasone, IGF-I and GH on Rat Organ Weights

STUDY A

| | Control | | | Dexamethasone | | |
|---|---|---|---|---|---|---|
| | Excipient | IGF-I | GH | Excipient | IGF-I | GH |
| Kidneys (mg) | 2290 ± 320 | 2440 ± 180$^{a,\,b,\,c}$ | 2270 ± 230 | 2030 ± 160$^a$ | 2090 ± 120$^b$ | 1960 ± 22$^c$ |

STUDY B

| | Control* | | Dexamethasone | | | |
|---|---|---|---|---|---|---|
| | Excipient | Excipient | IGF-I 0.8 mg/kg | IGF-I 2.4 mg/kg | GH 0.8 mg/kg | GH 2.4 mg/kg |
| Kidney (mg) | 1060 ± 101$^{a,\,b,\,c}$ | 833 ± 90$^a$ | 1010 ± 50 | 1050 ± 80 | 812 ± 35$^b$ | 780 ± 50$^c$ |

Statistics
$^a$identical letters in a row indicates two groups differ
Mean ± SD (n = 8 for Study A & 6 for Study B)

Treatment with GH or IGF-I had no impact on the kidney weights in either the excipient or dexamethasone-treated groups. The effect of dexamethasone, IGF-I, and GH on rat kidney-to-body weight ratio is shown in Table 4. The kidney:body weight ratios generally reflect the relative kidney weight changes.

doses of IGF-I further increased the kidney-to-body weight ratio in these dexamethasone-treated groups.

IGF-I stimulated the kidney (Study B) to gain a portion of the weight lost during dexamethasone treatment. Fagin et al., supra, reported that a week of dexamethasone or dexamethasone plus IGF-I had no effect on the

TABLE 4

The Effect of Dexamethasone, IGF-I and GH on Rat Organ to Body Weight Ratio ($\times 10^{-3}$)

STUDY A

| | Control | | | Dexamethasone | | |
|---|---|---|---|---|---|---|
| | Excipient | IGF-I | GH | Excipient | IGF-I | GH |
| Kidneys/BW | 7.79 ± 1.07 | 8.30 ± 0.67 | 7.71 ± 0.75 | 7.81 ± 0.68 | 8.29 ± 0.58 | 7.64 ± 0.71 |

STUDY B

| | Control Excipient | Excipient | IGF-I 0.8 mg/kg | IGF-I 2.4 mg/kg | GH 0.8 mg/kg | GH 2.4 mg/kg |
|---|---|---|---|---|---|---|
| | | | Dexamethasone | | | |
| Kidney/BW | 3.85 ± 0.28* | 4.46 ± 0.51$^{a,\,b}$ | 5.16 ± 0.23$^{a,\,c}$ | 5.09 ± 0.38$^{b,\,e,\,f}$ | 4.48 ± 0.29$^{c,\,e}$ | 4.59 ± 0.20$^{d,\,f}$ |

Statistics
$^a$identical letters in a row indicate two groups differ
*all Dex values differ from control
Mean ± SD (n = 8 for Study A & 6 for Study B)

The kidney-to-body weight ratios did not differ between the various treatment groups.

Study B

The data in Table 3 demonstrate that the control kidney weights are slightly less than those in Study A, reflecting the lower average body weights in this two-week study. Dexamethasone reduced the size of the kidney. IGF-I treatment recovered all of the kidney kidney, similar to the results of Study A after a week. However, the increased dexamethasone dose and treatment time of Study B revealed a significant effect of dexamethasone to reduce kidney weight. This was fully reversed by both doses of IGF-I, but was unaffected by GH.

C. Serum Constituents at Sacrifice

Table 5 shows the level of serum components in the sacrificed rats for Studies A and B.

TABLE 5

The Effect of Dexamethasone, IGF-I and GH on Serum Glucose, Protein and Triglycerides

STUDY A

| | Control | | | Dexamethasone | | |
|---|---|---|---|---|---|---|
| | Excipient | IGF-I | GH | Excipient | IGF-I | GH |
| Total IGF-I (ng/ml) | 730 ± 82$^{a,\,b}$ | 837 ± 118$^c$ | 541 ± 89$^{a,\,c,\,e,\,f}$ | 700 ± 106$^{d,\,e}$ | 875 ± 139$^{b,\,f,\,g}$ | 412 ± 123$^{\#}$ |
| Insulin (ng/ml) | 2.32 ± 1.64$^e$ | 1.89 ± 1.50$^e$ | 2.61 ± 1.36$^e$ | 7.77 ± 0.60$^a$ | 4.27 ± 2.46$^{a,\,b}$ | 7.32 ± 1.19$^b$ |
| Glucose (mg/dL) | 155 ± 43 | 152 ± 16 | 143 ± 21 | 183 ± 27 | 159 ± 26 | 164 ± 25 |
| Total Protein (gm/dL) | 6.74 ± 0.52$^{a,\,c}$ | 6.82 ± 0.98$^{b,\,d}$ | 7.59 ± 0.56$^{a,\,b}$ | 7.55 ± 0.29$^{c,\,d}$ | 7.03 ± 0.41 | 9.46 ± 0.68$^{\#}$ |
| Triglycerides (mg/dL) | 125 ± 34 | 110 ± 35$^{a,\,b}$ | 163 ± 45$^a$ | 166 ± 49$^b$ | 133 ± 30 | 213 ± 57$^{\#}$ |

TABLE 5-continued

The Effect of Dexamethasone, IGF-I and GH on Serum Glucose, Protein and Triglycerides

| | | STUDY B | | | | |
|---|---|---|---|---|---|---|
| | | | Dexamethasone | | | |
| | Control Excipient | Excipient | IGF-I 0.8 mg/kg | IGF-I 2.4 mg/kg | GH 0.8 mg/kg | GH 2.4 mg/kg |
| Total IGF-I (ng/ml) | 569 ± 131* | 341 ± 96 | 493 ± 83* | 552 ± 224* | 302 ± 21 | 290 ± 45 |
| Total Protein (gm/dL) | 7.43 ± 1.01[a, b] | 8.65 ± 0.88 | 8.37 ± 1.19[c] | 8.32 ± 1.34[d] | 10.1 ± 2.7[a] | 11.1 ± 1.7[b, c, d] |
| Triglycerides (mg/dL) | 173 ± 56[a] | 219 ± 67[b] | 224 ± 103 | 161 ± 71[c] | 505 ± 209[#] | 401 ± 127[a, b, c] |

Statistics
[a]identical letters in a row indicate two groups differ
*different from Dex-Excipient and both GH groups
[#]different from all other groups
*all Dex values differ from control
Mean ± SD (n = 8 for Study A & 6 for Study B)

As indicated in Table 5, dexamethasone treatment alone did not alter serum IGF-I levels in Study A. However, the IGF-I infusion elevated the serum IGF-I levels by 20%, indicating that the minipump delivered up to the end of the study. Continuous GH infusion in both control and dexamethasone-treated groups significantly reduced total IGF-I by 35–41%.

In Study B, the decreased serum IGF-I and the lack of a GH effect in the dexamethasone-treated group is likely due to the longer duration of the study or the increased dose of dexamethasone. As in Study A, both doses of IGF-I elevated circulating total IGF-I levels in Study B.

Serum insulin levels at sacrifice were markedly reduced in the IGF-I-treated group of Study A relative to the excipient controls, suggesting an insulin sparing effect. In contrast, with GH there was a trend toward potential hyperinsulinemia, a well recognized diabetogenic result of GH administration in normal mammals. A similar trend was seen in the glucocorticoid-treated animals. The glucose levels at sacrifice were similar in Study A. High-dose glucocorticoids as administered during these studies can induce similar carbohydrate intolerance and insulin resistance in man (Olefsky and Kimmerling, Am. J. Med. Sci., 271: 202–210 (1976)). The ketamine/rhompin anesthesia used in Study B disallowed glucose measurements.

Total protein and triglycerides were elevated in the dexamethasone plus GH-treated rats. IGF-I treatment had no impact on total serum protein, but tended to reduce the triglyceride levels relative to the GH alone (Study A) or GH+dexamethasone (Studies A and B) groups. Both corticosteroid and GH excess are associated with hyperlipidemia in humans.

In summary, IGF-I infusion enhanced body weight gain at sacrifice of glucocorticoid-treated animals and enhanced their kidney weight when they were treated with higher doses of lucocorticoid (e.g., 1.0 mg of dexamethasone per liter of water) and/or treated with glucocorticoid for longer periods of time. The magnitude of the body weight gain (>20 g) with the high dose of IGF-I, and its maintenance for 14 days, suggests that IGF-I is having a significant effect in the dexamethasone-treated rats.

In contrast, GH infusion ultimately depressed further the body weight decrement caused by dexamethasone, and had little or no effect on the kidney at sacrifice.

These data stand in contrast to the significant weight gain response to recombinant human GH and IGF-I that occurs in another model of growth failure, namely, that of GH deficiency due to hypophysectomy (Guler et al., N. Eng. J. Med., 317: 137 (1987); Moore et al., Endocrinology, 122: 2920–2926 (1988)) or that of a genetic defect in GH production as in the dwarf rat (Skottner et al., supra). IGF-I is superior to GH in counteracting the catabolic state imposed by chronic glucocorticoid therapy.

EXAMPLE II

Glucocorticoid excess in children, whether due to cortisol-secreting adrenal tumors or hypersecretion of adreno-corticotrophic hormone, has been well documented to result in growth failure. MacArthur et al., Mayo Clin. Proc., 47: 318–326 (1972); Kaplan, Clin. Pediatric and Adolescent Endocrinology, Chap. p. 11, (1982); Preece, Post. Grad. Med. J., 52: 625 (1976); Murray et al., Lancet, 11: 197 (1976); Chesney et al., Am. J. Dis. Child., 132: 768 (1978). In asthmatic children on prednisone, studies have reported 20–30 percent of children were two or more standard deviations below the mean for height, which is more than ten times as many as would be expected in the general pediatric population.

In addition, there are a variety of medical conditions that are currently treated with glucocorticoids for immunosuppressive and antiinflammatory effects (i.e., juvenile rheumatoid arthritis, inflammatory bowel disease, severe asthma, and other allergic conditions). These conditions of exogenous glucocorticoid excess may also result in growth failure. Growth hormone secretion and levels of immunoreactive IGF-I are generally normal in conditions of endogenous or exogenous glucocorticoid excess, and treatment with GH is not of proven benefit. Strickland et al., Am. J. Dis. Child., 123: 207–213 (1972)

Although most children with Cushing's syndrome experience some "catch up" growth after resolution of their hypercortisolism, this is usually insufficient to regain the lost height. Important determinants of the potential for catch-up growth appear to be the duration and intensity of glucocorticoid exposure and the age of the patient. Solomon and Schoen, Am. J. Dis. Child., 130: 200–202 (1976); Mosier et al., Am. J. Dis. Child., 124: 251–253 (1972) Growth impairment resulting from supraphysiologic doses of glucocorticoids may be minimized by decreasing the dose or changing to an alternate day dosing regimen. Soyka, Am. J. Dis. Child., 113: 693–701 (1967). However, this is not always possible.

An example of a clinical experience is depicted in the accompanying FIG. 2, where patient K.T.P. was growing normally at the 25th percentile. After progressive renal insufficiency, the patient underwent renal transplantation and was treated with supraphysiologic doses of glucocorticoids for immunosuppression. The growth rate slowed dramatically. Even after administration of recombinant GH (0.05 mg/kg/day by subcutaneous injection), the growth rate failed to approach the normal curve.

In contrast, based on the preclinical results with a pertinent rat model described above, IGF-I would be a more effective therapeutic agent for growth restoration and, additionally, does not exhibit the potential diabetogenic activity of GH.

Another clinical setting where IGF-I would be expected to be useful would be to treat steroid-dependent asthmatic children. As in children after renal transplantation, IGF-I administration would be expected to improve growth, antagonize the diabetogenic effect of glucocorticoids (a situation that in the long term would be exacerbated by the alternative therapy with GH), and also potentially minimize osteopenic effects of excessive glucocorticoids.

What is claimed is:

1. A method for at least partially restoring normal growth, weight gain, and lean body mass of a mammal with glucocorticoid excess comprising administering to the mammal an effective amount of IGF-I.

2. The method of claim wherein the mammal is a non-adult mammal.

3. The method of claim 1 wherein the mammal is human.

4. The method of claim 2 wherein the mammal is human.

5. The method of claim 3 wherein the IGF-I is human IGF-I.

6. The method of claim 5 wherein the IGF-I is native-sequence, mature IGF-I or an IGF-I analog having the glutamic acid at position 3 replaced by another amino acid or deleted.

7. The method of claim 6 wherein the IGF-I is brain IGF-I.

8. The method of claim 1 wherein the IGF-I is formulated in a pharmaceutical carrier.

9. The method of claim 8 wherein the IGF-I is in a sterile, isotonic solution.

10. The method of claim 1 wherein the administration is by continuous infusion.

11. The method of claim 1 wherein the administration is by a subcutaneous or intravenous route.

12. The method of claim 1 wherein the effective amount is at least 0.5 mg/kg/day.

13. The method of claim 3 wherein the effective amount is at least 1 mg/kg/day.

14. The method of claim 1 wherein the glucocorticoid excess results from chronic treatment of the mammal with a glucocorticoid.

15. The method of claim 14 wherein the glucocorticoid is dexamethasone.

* * * * *